US006383511B1

(12) United States Patent
Cassel

(10) Patent No.: US 6,383,511 B1
(45) Date of Patent: May 7, 2002

(54) LOCAL PREVENTION OR AMELIORATION OF PAIN FROM SURGICALLY CLOSED WOUNDS

(75) Inventor: R. Douglas Cassel, Harrisburg, PA (US)

(73) Assignee: EpiCept Corporation, Englewood Cliffs, NJ (US)

( * ) Notice: Subject to any disclaimer, the term of this patent is extended or adjusted under 35 U.S.C. 154(b) by 0 days.

(21) Appl. No.: 09/425,925

(22) Filed: Oct. 25, 1999

(51) Int. Cl.[7] .................... A61F 13/00; A61K 9/70; A61K 31/245
(52) U.S. Cl. ........................... 424/449; 424/448
(58) Field of Search .................. 424/448, 449

(56) References Cited

U.S. PATENT DOCUMENTS

| | | | |
|---|---|---|---|
| 3,814,095 A | | 6/1974 | Lubens |
| 4,210,670 A | | 7/1980 | Cooke |
| 4,366,243 A | | 12/1982 | Rupchock et al. |
| 4,615,699 A | | 10/1986 | Gale et al. |
| 4,751,087 A | | 6/1988 | Wick |
| 4,765,986 A | | 8/1988 | Liedtke |
| 4,769,038 A | * | 9/1988 | Bendavid et al. ............. 623/13 |
| 5,122,155 A | * | 6/1992 | Eberbach ..................... 606/213 |
| 5,272,139 A | * | 12/1993 | Cary ........................... 514/171 |
| 5,282,788 A | * | 2/1994 | Wilk et al. .................. 604/540 |
| 5,330,452 A | | 7/1994 | Zook |
| 5,332,576 A | | 7/1994 | Mantelle |
| 5,366,460 A | * | 11/1994 | Eberbach ..................... 606/151 |
| 5,411,738 A | * | 5/1995 | Hind ........................... 424/445 |
| 5,415,866 A | | 5/1995 | Zook |
| 5,417,671 A | | 5/1995 | Jackson |
| 5,466,465 A | | 11/1995 | Royds et al. |
| 5,601,838 A | * | 2/1997 | Hind ........................... 424/449 |
| 5,618,563 A | * | 4/1997 | Berde et al. ................. 424/501 |
| 5,700,485 A | * | 12/1997 | Berde et al. ................. 424/501 |
| 5,760,077 A | * | 6/1998 | Shahinian .................... 514/540 |
| 5,776,952 A | | 7/1998 | Liedtke |
| 5,810,786 A | | 9/1998 | Jackson et al. |
| 5,827,529 A | | 10/1998 | Ono et al. |
| 5,840,755 A | | 11/1998 | Liedtke |
| 5,863,941 A | | 1/1999 | Liedtke |
| 5,916,583 A | * | 6/1999 | Broberg et al. .............. 424/426 |
| 5,919,479 A | | 7/1999 | Zhang et al. |
| 5,922,026 A | * | 7/1999 | Chin ............................ 623/11 |
| 5,922,340 A | * | 7/1999 | Berde et al. ................. 424/426 |
| 5,942,241 A | * | 8/1999 | Chasin et al. ................ 424/426 |
| 5,948,389 A | * | 9/1999 | Stein ............................ 424/45 |
| 5,976,547 A | * | 11/1999 | Archer et al. ................ 424/742 |
| 5,993,836 A | * | 11/1999 | Castillo ....................... 424/401 |
| 6,007,843 A | * | 12/1999 | Orizen et al. ................ 424/488 |
| 6,046,187 A | * | 4/2000 | Berde et al. ................. 514/180 |
| 6,143,278 A | * | 11/2000 | Elkhoury ...................... 424/45 |
| 6,217,911 B1 | * | 4/2001 | Vaugn et al. ................ 424/501 |
| 6,238,702 B1 | * | 5/2001 | Berde et al. ................. 424/489 |
| 6,299,902 B1 | * | 10/2001 | Jun et al. ..................... 424/449 |

OTHER PUBLICATIONS

Berkovitch et al., 1995, "Use of a Eutectic Mixture of Local Anesthetics for Prolonged Subcutaneous Drug Administration", J. Clin. Pharmacol. 35:295–297.

Cassel, 1998, "A Model Managed Care Hernia Clinic", Hernia 2(Suppl. 1):S7 (abstract #24; presented at the 1998 Annual Meeting of the American Hernia Society, Miami, FL, Feb. 6–8, 1998).

Cassel, 1998, "A Model–Managed Care Hernia Clinic", abstract/poster presented at the American College of Surgeons Clinical Congress, Orlando, FL, Oct. 26, 1998.

Cassel, 1999, "A Model–Managed Care Hernia Clinic", Hernia 3(Suppl. 1):S18 (abstract #79; presented at the 1999 Annual Meeting of the American Hernia Society, Las Vegas, NV, Feb. 22–24, 1999).

Filos and Lehmann, 1999, "Current Concepts and Practice in Postoperative Pain Management: Need for a Change?", Eur. Sur. Res. 31:97–107.

Juhlin et al., "A Lidocaine–Prilocaine Cream for Superficial Skin Surgery and Painful Lesions", Acta Dermato–venereologica 60:544–546.

Lubens et al., 1974, "Anesthetic Patch for Painful Procedures Such As Minor Operations", Am J. Dis. Child 128:192–194.

McCafferty et al., 1988, "Comparative in vivo and in vitro Assessment of the Percutaneous Absorption of Local Anesthetics", Br. J. Anaesth. 60:64–69.

Russo et al., 1980, "Lidocaine Anesthesia: Comparison of Iontophoresis, Injection and Swabbing", Am. J. Hosp. Pharm. 37:843–847.

Sarpotdar and Zatz, 1986, "Evaluation of Penetration Enhancement of Lidocaine by Nonionic Surfactants Through Hairless Mouse Skin In Vitro", J. Pharmaceut. Sci. 75:176–181.

* cited by examiner

Primary Examiner—Shep K. Rose
(74) Attorney, Agent, or Firm—Pennie & Edmonds LLP

(57) ABSTRACT

A non-invasive and non-systemic method for intradermal prevention OR amelioration of pain from a surgically closed wound is disclosed. The method comprises topical delivery of a local anesthetic to an exterior surface of a surgically closed wound.

10 Claims, No Drawings

LOCAL PREVENTION OR AMELIORATION OF PAIN FROM SURGICALLY CLOSED WOUNDS

FIELD OF THE INVENTION

The present invention relates to a local method to prevent or ameliorate the pain associated with surgical incision by topically administering a local anesthetic.

BACKGROUND OF THE INVENTION

The skin is a complex multilayer organ with a total thickness of 2–3 mm. The panniculus adiposus, a variably thick fatty layer, is below the dermis. The dermis is a layer of dense connective tissue that supports the epidermis. The epidermis comprises a layer of epithelial cells and is about 100 $\mu$m thick. The epidermis is further classified into a number of layers, of which the outermost layer is the stratum corneum (15–20 $\mu$m thick). The stratum corneum comprises highly dense, keratinized tissue and is the skin's main source of penetration and permeation resistance (Montagna, W. and Parakkal, P. F. (1974) *The Structure and Function of Skin*, Academic Press, New York and Holbrook, K. A. and Wolf, K. (1993) The Structure and Development of Skin, In: *Dermatology in General Medicine*, Vol 1, 4th ed., Eds. T. B. Fitzpatrick, A. Z. Eisen, K. Wolff, I. M. Feedberg, and K. F. Austen, McGraw Hill, Inc., New York, pp. 97–145).

Because of the skin's drug permeation resistance, as little as about 1 percent and usually no more than about 15 percent of a drug in a dermatological formulation is bioavailable (Ghosh, T. K.; Pfister, W. R.; Yum, S. I. *Transdermal and Topical Drug Delivery Systems*, Interpharm Press, Inc. p. 7).

After a surgical procedure, pain results from pain receptor stimulation. Postoperative or post-traumatic pain is caused by stimulation of sub-dermal sensory nerve receptors (i.e., nociceptors). And trauma is increased over the first 24–48 hours by phases of reactive edema and by release of cytokines and chemo reactive agents.

After a wound is closed by a surgical professional, pain prevention options are limited, especially outpatient pain control and management. Traditionally, for post wound closure pain prevention, opiates and NSAIDs are administered systemically, i.e., throughout the organism via the circulatory system. Topical intradermal pain prevention has seen little application, likely because surgically closed wounds are expected to present a drug permeation barrier similar to intact skin.

Systemic administration of pain relief drugs usually is effected orally or intravenously, The AHCPR Guidelines suggested pain control options include: systemic administration of non-steroidal anti-inflammatory drugs (NSAIDs) or opiates using the traditional "as needed" schedule or around-the-clock administration (American Pain Society, 1989).

Systemic pharmacotherapies are, however, accompanied by adverse side effects, particularly with continuous use. With NSAIDs, there is a high risk of gastric disorders, erosions of the stomach lining and the intestinal mucus membrane and bleeding. Administration of opiates and narcotics presents a high dependency risk aside from other undesirable effects, like, respiratory depression, sedation, dizziness, nausea, and constipation. Furthermore, systemic use of these substances while taking other medications can result in detrimental pharmacologic interactions. Of course, pharmacological interactions become more significant in an ambulatory postoperative patient for whom polypharmacy is necessary.

In contrast to prevention of pain with systemic agents, pain can also be treated locally, that is, by delivering the pain reliever directly to the painful area. Thus, for example, a local anesthetic or NSAID might be injected at the pain area.

Local anesthetics reversibly block impulse conduction along nerve axons and other excitable membranes that utilize sodium channels as the primary means of action potential generation. This blocking action can be used clinically to block pain sensation at specific areas of the body (Strichartz, G. R. (Ed.) Local Anesthetics, Handbook of Experimental Pharmacology, Vol. 81, Springer, Berlin/New York, 1987). Furthermore, local anesthetics generally possess a good tissue tolerance, and in some cases, local anesthetics have bactericidal properties, and may impart a positive influence on the regional vessel innervation during wound healing and episodes of.

Traditionally, pain relief with local anesthetics—at least for the more painful wounds, such as surgically closed wounds—involves injection into the area of the nerve fibers to be blocked (Jones M. Gregg AK, Anaesthesia 1999 February; 54(2):200). But with this therapy, the medical professional is confronted with the risk/benefit consideration between the negative effects of systemic absorption versus achieving pain relieving concentrations at the pain site. Systemic absorption of injected local anesthetics is modified by several factors, including dosage, injection site, drug tissue binding. For example, local anesthetic injection to a highly vascular area results in more rapid systemic absorption and thus, adversely, higher drug blood levels are attained. In an analogy to injection, local anesthetics have also been infused directly into open wounds before surgical closure (e.g., U.S. Pat. Nos. 5,272,139 and 5,922,340).

In addition to systemic absorption risk, local injection is painful and invasive and also requires professional administration. Of course, with surgically closed wounds, which are very sensitive, injections should be avoided if possible.

While topical application of local anesthetics might overcome some of the problems associated with injection (especially systemic dangers), this method has not been widely used, mainly, as discussed above, by the difficulty to get significant concentrations through skin barrier. Further advantages of topical administration include improved patient compliance and reversible action (i.e., the action can be reversed by removing the anesthetic from the application site) (Ghosh, T. K.; Pfister, W. R.; Yum, S. I. *Transdermal and Topical Drug Delivery Systems*, Interpharm Press, Inc. pp. 33–112).

Thus, topical administration of local anesthetics has, in general, only been used to treat minor pain where small concentrations of the anesthetic will suffice. For example, for relief of minor pain from scrapes, skin irritations. Topical administration of local anesthetics is also indicated for topical anesthesia prior to needle insertion (e.g., blood sampling, vaccination, allergy testing), and superficial surgical procedures (Zook et al. U.S. Pat. No. 5,415,866; Royds, R. B. U.S. Pat. No. 5,466,465; Zhange et al. U.S. Pat. No. 5,919,479; and Berkovitch, et al. *J. Clin. Pharmacol.* 35: 295–297).

In addition to classic local anesthetics—i.e., amide and ester type—several of the more potent NSAIDs have been developed into topical products for local application to minor pain sites—for example, Cordran® Tape delivers flurandrenolide for relief of inflammatory and puritic conditions (Oclassen (1995) Cordon Tape Package Insert, Oclassen Pharmaceutical, San Rafael, Calif.).

But, in brief, topical application of local anesthetics is not known to treat the more intense pain associated with wounds after surgical closure. This is likely because a surgically closed wound is expected to present the same permeability difficulties associated with intact skin.

Surgically closed wounds are tightly welded. The most common techniques for closure of open wounds is suturing (with either non-absorbable and absorbable materials) and stapling. These mechanical closure methods provide tension on the skin tissue at the wound border that encourages epithelial tissue to migrate toward the wound and cover it. As the skin heals, the wound becomes even more impenetrable by pharmaceuticals, nonetheless, the pain persists. Also, modern surgical suturing techniques and intraoperative hemostasis, wound treatment has been greatly advanced by the use of suitable supplementary materials, such as tissue glues and adhesives, to accelerate hemostasis as well as to optimize conditions and control of wound closure. Fibrin-based biological glues have proven particularly advantageous over non-biological adhesives because fibrin-based glues mimic the natural coagulation cascade and enhance the healing process.

In short, surgically closed wounds are expected to present a formidable barrier against penetration of topically applied pain relief agents in sufficient concentration to relived the intense pain once the original anesthetic (systemic or locally injected) used in the surgery has worn off.

Thus far a non-invasive and non-systemic treatment for pain resulting from surgically closed wounds—e.g., closed wounds, wherein the wound resulted from a surgical procedure, such as laporasopy or any non-surgical occurrence, such as, accidental knife cuts, etc.—has not been available.

SUMMARY OF THE INVENTION

The present invention concerns a non-invasive and non-systemic method for prevention or amelioration of incisional pain resulting from a surgically closed wound. The inventors have found that topically applied local anesthetics can be used to treat the pain associated with a surgically closed wound.

In one embodiment the invention comprises, a method of preventing pain from a surgically closed wound in a subject comprising applying a pharmaceutically acceptable topical drug formulation comprising a therapeutically effective dose of a local anesthetic or a pharmaceutically acceptable salt thereof on or adjacent to an exterior surface of the wound. The wound can be any wound such as an accidental knife cut, preferably the wound resulted from a surgical procedure.

In a preferred embodiment the method of the invention may be used to prevent the pain from surgically closed wounds resulting from laparoscopy, hemiaplasty, breast biopsy, or excision of subcutaneous tumors.

Any local anesthetic can be used with the current invention. Preferred local aesthetics include lidocaine, tetracaine, bupivacaine, prilocaine, mepivacaine, procaine, chloroprocaine, ropivacaine, dibucaine, etidocaine, or benzocaine or any mixtures thereof The most preferred local anesthetic is lidocaine.

In another embodiment, the current invention concerns a patch comprising a local anesthetic in an amount therapeutically effective to prevent or ameliorate pain from a surgically closed wound in a mammal suffering from the pain packaged in association with instructions, the instructions comprising: applying the patch to the surgically closed wound such that the patch covers at least a part of the area of the surgically closed wound.

These and other features, aspects, and advantages of the invention will become better understood with reference to the following detailed description, example, and appended claims.

DETAILED DESCRIPTION OF THE PREFERRED EMBODIMENTS

The present invention may be used to prevent or ameliorate pain from any surgically closed wound by topically applying a local anesthetic in a pharmaceutically acceptable topical drug formulation. The pharmaceutically acceptable topical drug formulation may be contained in a patch.

According to the invention the term "subject" means any mammal, including domesticated mammals, like dogs and cats. Preferably, the subject is a human.

As used herein, the term "local anesthetic" means any drug that provides local numbness or analgesia or any drug that provides a regional blockage of nociceptive pathways (afferent and/or efferent). The meaning of "local anesthetic" also encompasses drugs not traditionally associated with local anesthetic properties but which have a local anesthetic effect, like NSAIDs (e.g., acetylsalicylic acid, ketoprofen, piroxicam, diclofenac, indomethacin, ketorolac, Vioxx®, and Celebrex®), opioids as described in U.S. Pat. No. 5,589,480 (e.g., morphine or morphine sulfate), and other agents.

The local anesthetic can be any local anesthetic known or to be developed. The amide and ester type local anesthetics are preferred. Amide type local anesthetics are characterized by an amide functionality, while ester type local anesthetics contain an ester functionality. Preferred amide type local anesthetics are: lidocaine, bupivacaine, prilocaine, mepivacaine, etidocaine, ropivacaine, dibucaine, and mixtures thereof. Preferred ester type local anesthetics are: tetracaine, procaine, benzocaine, chloroprocaine, and any mixture thereof. The most preferred local anesthetic is lidocaine.

When the local aesthetic contains a basic functionality, it may be present in the form of an acid addition salt or as the free base. Preferred salts are the hydrochloride, bromide, acetate, citrate, carbonate or sulfate salts. But preferably, the local anesthetic agent is in the form of a free base. More preferably lidocaine is used in the free base form.

Furthermore, in order to improve the effectiveness and tolerance of the present topically effective therapy, local anesthetics with different pharmacodynamics and pharmacokinetics may be combined in a pharmaceutically acceptable topical drug formulation. A preferred combination of local anesthetics is lidocaine and prilocaine and another preferred combination is lidocaine and tetracaine.

The term "surgically closed wound", as used herein, means any wound that has been closed, such that, the opposing edges of skin—which comprise the wound—have been joined together by a device or material. Preferably, the wound has been closed by a medical professional, such as, a surgeon, doctor, doctors assistant, emergency medical technician, or nurse.

Surgically closed wounds include but are not limited to wounds that have been closed with: sutures (absorbable or non-absorbable, synthetic or natural), staples, and biological glues.

The term "topical drug formulation" means a formulation designed for topical skin application and containing a drug, for example, a formulation in the form of a polymer matrix, cream, gel, emulsion, or ointment.

Application is accomplished by applying the topical drug formulation on or adjacent to an exterior surface of the surgically closed wound. Preferably the topical drug formulation is applied directly to the surface of the surgically closed wound. The pharmaceutically acceptable topical drug formulation of the invention should be applied using a sterile technique.

The term "drug" means a substance used in the diagnosis, treatment, or prevention of a disease or medical condition or an active component of a medication. Of course, the term "drug" encompasses local anesthetics.

As used herein "patch" comprises at least a topical drug formulation and a covering layer, such that, the patch can be placed over the surgically closed wound thereby positioning the patch/drug formulation adjacent to the wound's surface. Preferably the patch is designed to maximize drug delivery through the stratum corneum, upper epidermis, and into the dermis, and to minimize absorption into the circulatory system, reduce lag time, promote uniform absorption, and reduce mechanical rub-off.

The topical drug formulations and patch systems according to the invention preferably provide controlled release of a local anesthetic agent to the surgically closed wound.

In one embodiment of the invention, the topical drug formulation comprises a carrier system. Pharmaceutically effective carriers include buffered solutions, e.g, hypotonic or buffered saline, liposomes and the like or any other art-known pharmaceutically acceptable topical carrier. More preferred carriers include creams, ointments, oils, plasters, and emulsions. A more complete listing of art-known carriers is provided by reference texts that are standard in the art, for example, *Remington's Pharmaceutical Sciences*, 16th Edition, 1980 and 17th Edition, 1985, both published by Mack Publishing Company, Easton, Pa., the disclosures of which are incorporated by reference herein in their entireties.

After application of the topical drug formulation to the surgically closed wound, the wound may be covered with a dressing. The term "dressing", as used herein, means a covering designed to protect a previously applied drug formulation. "Dressing" includes coverings such as a bandage, which may be porous or non-porous and various inert coverings, e.g., a plastic film wrap or other non-absorbent film. The term "dressing" also encompasses non-woven or woven coverings, particularly elastomeric coverings, which allow for heat and vapor transport. These dressings allow for cooling of the pain site, which provides for greater comfort.

In a preferred embodiment of the current invention, the topical drug formulation containing a local aesthetic is contained in a patch that is applied adjacent to the surface of the surgically closed wound. Preferably, the patch components resemble the viscoelastic properties of the skin and conform to the skin during movement to prevent undue shear and delamination.

A patch containing a topical drug formulation has advantages over the simple topical drug formulation alone. One advantage is that the dose is controlled by the patch's surface area. Other advantages of patches are constant rate of delivery, longer duration of action (the ability of to adhere to the skin for 1, 3, 7 days or longer); improved patient compliance, non-invasive dosing, and reversible action (i.e., the patch can simply be removed).

A patch suitable for use with the invention should contain at least: (1) a backing layer and (2) a carrier formulated with a local anesthetic.

Preferred patches include (1) the matrix type patch; (2) the reservoir type patch; (3) the multi-laminate drug-in-adhesive type patch; and (4) the monolithic drug-in-adhesive type patch; and (Ghosh, T. K.; Pfister, W. R.; Yum, S. I. *Transdermal and Topical Drug Delivery Systems*, Interpharm Press, Inc. p. 249–297, incorporated herein by reference). These patches are well known in the art and generally available commercially.

For practice of the invention, the matrix type and the drug-in-adhesive type patches are especially preferred. The more preferred drug-in-adhesive patch is the monolithic type.

The matrix patch comprises an anesthetic containing matrix, an adhesive backing film overlay, and preferably, a release liner. In some cases, it may be necessary to include a impermeable layer to minimize drug migration into the backing film (e.g., U.S. Pat. No. 4,336,243, incorporated herein by reference). The anesthetic containing matrix is held against the skin by the adhesive overlay. Examples of suitable anesthetic matrix materials include but are not limited to lipophilic polymers, such as polyvinyl chloride, polydimethylsiloxane, and hydrophilic polymers like polyvinylpyrrolidone, polyvinyl alcohol, hydrogels based on gelatin, or polyvinylpyrrolidone/polyethylene oxide mixtures.

The reservoir type patch design is characterized by a backing film coated with an adhesive, and a reservoir compartment containing a drug formulation preferably, in the form of a solution or suspension, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the wound.

The monolithic drug-in-adhesive patch design is characterized by the inclusion of the drug formulation in the skin contacting adhesive layer, a backing film and preferably, a release liner. The adhesive functions both to release the anesthetic and adhere the anesthetic matrix to the skin. The drug-in-adhesive system does not require an adhesive overlay and thus the patch size is minimized. Also, drug-in-adhesive type patches are thin and comfortable (e.g., U.S. Pat. No. 4,751,087, incorporated herein by reference).

The multi-laminate drug-in-adhesive patch design further incorporates additional semi-permeable membrane between two distinct drug-in-adhesive layers or multiple drug-in-adhesive layers under a single backing film (Peterson, T. A. and Dreyer, S. J. Proceed. *Intern. Symp. Control Rel. Bioact. Mater.* 21: 477–478, incorporated herein by reference).

Semi permeable membranes, useful with the reservoir or multi-laminate patch, include thin non-porous ethylene vinyl acetate films or thin microporous films of polyethylene employed in microlaminate solid state reservoir patches.

Adhesives for use with the drug-in-adhesive type patches are well known in the art and selection is readily accomplished by an ordinary practitioner. Three basic types commonly used are polyisobutylenes, silicones, and acrylics. Adhesives useful in the present invention can function under a wide range of conditions, such as, high and low humidity, bathing, sweating etc. Preferably the adhesive is a composition based on natural or synthetic rubber, polyacrylate, polyvinylacetate, polybutylacrylate, polymethylacrylate, polydimethylsiloxane, and hydrogels (e.g., high molecular weight polyvinylpyrrolidone and oligomeric polyethylene oxide). The most preferred is polyacrylate.

Suitable release liners include but are not limited to occlusive, opaque, or clear polyester films with a thin coating of pressure sensitive release liner (e.g., siliconefluorsilicone, and perfluorcarbon based polymers.

Backing films may be occlusive or permeable and are derived from synthetic polymers like polyolefin oils polyester, polyethylene, polyvinylidine chloride, and polyurethane or from natural materials like cotton, wool, etc. Occlusive backing films, such as synthetic polyesters, result in hydration of the outer layers of the stratum corneum while non-occlusive backings allow the area to breath (i.e., promote water vapor transmission from the skin surface). More preferably the backing films are occlusive and comprised of a polyolefin oil.

Additionally, in order to make the present therapy safer, use-specific, and more manageable overall, the present patch may have such a geometric shape such that it corresponds to the special conditions of the application field. Thus, the shape of the patch can be flat or three-dimensional, round, oval, square, and have concave or convex outer shapes, or the patch or bandage can also be segmented by the user into corresponding shapes with or without additional auxiliary means.

Selection of the appropriate dosage for the application site is an important consideration. The rate of intradermal anesthetic delivery from the topical drug formulation or patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum (Wester, R. C. and Maibach, H. I. (1989) Regional variation in Percutaneous Absorption: *In Percutaneous Absorption, Mechanism, Methodology, Drug Delivery*, $2^{nd}$ed., Eds. R. L. Bronaugh and H. I. Maibach, Marcel Dekker, Inc., New York, pp. 111–119 (incorporated herein by reference)). Of course, the dosages and dosing frequency will be determined by a trained medical professional, and will depend upon many factors such as wound location, size, severity, and the type of surgical closure.

Topical formulations in the form of a gel, cream, or ointment, containing the local anesthetic may be applied adjacent to the surgically closed wound such that the wound and a portion of its surrounding area are covered. The amount of local anesthetic in the topical drug formulation will generally be in the range of about 1 percent to about 25 percent (percents are by weight), preferably, in the range of about 2 percent to about 20 percent, most preferably about 3 percent to about 5 percent.

With gels, creams, or ointments, typically 1 to 4 applications are required per day. Generally, about 0.5 g/cm² to about 5 g/cm², preferably 1 g/cm² to about 2 g/cm² of the topical drug formulation is applied to and around the wound. Preferably a lidocaine topical formulation—wherein the lidocaine concentration is about 1 percent to about 10 percent, more preferably about 2 percent to about 5 percent—is applied to the surgically closed wound in an amount of about 1 g/cm² to about 2 g/cm² in the area of an and around the wound. After application, preferably, the wound is covered with a dressing.

When a combination of local anesthetics is used, the preferred combination is a eutectic mixture of lidocaine and prilocaine. In such a mixture, the amount of lidocaine can range from about 1 percent to about 40 percent, preferably from about 2 percent to about 20 percent, and more preferably from about 3 percent to about 5 percent and the amount of prilocaine can range from about 0.5 percent to about 40 percent, preferably from about 2 percent to about 20 percent, and more preferably about 3 percent to about 5 percent. Preferably the mixture is formulated as an oil in water emulsion.

Another preferred local aesthetic combination is a mixture of lidocaine and tetracaine. In such a mixture, the amount of lidocaine can range from about 1 percent to about 40 percent, preferably from about 2 percent to about 20 percent, and more preferably from about 3 percent to about 5 percent and the amount of tetracaine can range from about 0.5 percent to about 40 percent, preferably from about 2 percent to about 20 percent, and more preferably about 3 percent to about 5 percent. Preferably the mixture is formulated as an oil in water emulsion.

When a patch is used to relieve the pain from a surgically closed wound, the dosage of the local anesthetic required to achieve pain relief is determined by the active surface area of the medicated portion of the patch in direct contact with the skin. Several dosage strengths are advantageous depending upon the severity of the wound. In general, a physician may begin dosing with a low or intermediate strength patch and then, depending upon the effectiveness, adjust the dosage up or down by prescribing a patch of higher or lower anesthetic concentration or a patch of larger or smaller surface area, or, in some cases, multiple patches.

In general, the anesthetic will comprise from about 0.5 percent to about 40 percent by weight of the patch, preferably from about 10 percent to about 30 percent, more preferably from about 15 percent to about 25 percent, and most preferably from about 18 percent to about 22 percent by weight of the patch. Fresh patches may be applied multiple times per day, but, preferably, a fresh patch is applied about every 18 to about every 48 hours. More preferably, the patch is applied daily.

In another embodiment of the current invention, the local anesthetics used in the topical drug formulations and patches are in a form capable of transport into the dermis. Administration of these drug formulations according to the invention may involve the use of excipients. Any pharmaceutically acceptable excipient is suitable. For example, penetration enhancers, plasticisers, antioxidants, colorants, preservatives, antibiotics, etc.

The method of the invention may be used with other conventional systemic pain relief therapies, including but not limited to analgesics, opiates, and narcotics.

When practicing the invention, medicinal agents or their salts may be incorporated into the topical drug formulation or into the appropriate fraction or layer of the patch. For example, antifungal agents such as ciclopirox, chloroxylenol, triacetin, sulconazole, nystatin, undecylenic acid, tolnaftate, miconizole, clotrimazole, oxiconazole, griseofulvin, econazole, ketoconozole, and amphotericin B may be incorporated. Antibiotic agents such as mupirocin, erthromycin, clindamycin, gentamicin, polymyxin, bacitracin, silver sulfadiazine, and the like. Antiseptic agents such as iodine, Povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride likewise could be incorporated into the topical drug formulation or the patch. Furthermore, anti-inflammatories such as hydrocortisone, prednisone, triamcilolone, betamethasone, dexamethasone, and the like may be incorporated.

In another embodiment, penetration enhancers can be included in the topical drug formulation or patch, to optimize local anesthetic delivery into and through the skin (Ghosh, T. K. et al. (1993), *Pharm. Tech.* 17(3):72–98; Ghosh, T. K. et al. (1993), *Pharm. Tech.* 17(4): 62–89; Ghosh, T. K. et al. (1993), *Pharm. Tech.* 17(5):68–76). The penetration enhancer should be pharmacologically inert, non-toxic, and non-allergenic, have rapid and reversible onset of action, and be compatible with the drug formulation (Pfister et al. *Pharm. Tech.* 14(9):132–140, incorporated herein by reference).

Useful penetration enhancers include but are not limited to ethyl alcohol, isopropyl alcohol, or octolyphenylpolyethylene glycol. More preferred penetration enhancers include oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methyl pyrrolidone.

In yet another embodiment of the current invention, agents may be included to prolong the anesthetic effect, such as, a glucocorticosteroid (see, U.S. Pat. No. 5,922,340) or a vasoconstrictors, such as a catecolamine.

The present invention and its many attendant advantages will be understood from the foregoing description and it will be apparent that various changes in form, construction and arrangement of the parts there of may be made without departing from the spirit and scope of the invention or sacrificing all of its material advantages, the form hereinbefore described are merely exemplary embodiments thereof.

EXAMPLE 1

Tension free mesh hernia repair was performed on approximately 300 male and female patients with groin hernias. An approximately three inch long incision was made and the hernia was repaired with layered and subcuticular closure with absorbable sutures (vicril sutures) followed by application of a 4 percent lidocaine reservoir patch (see U.S. Pat. No. 4,765,986, incorporated herein by reference). A fresh patch was applied about every six hours for the first 48 hours after surgery and supplemental oral analgesics (ibuprofen, Darvocet®, Toradol®, or Vicodin®) were administered at the patient's discretion. The patients were interviewed concerning pain relief and the quantity of oral analgesics the patient required. About 85% of the patients reported minimal pain and little need for oral analgesics.

What is claimed is:

1. A method of preventing or ameliorating pain from a surgically closed wound in a subject comprising topically applying a pharmaceutically acceptable drug formulation comprising a therapeutically effective dose of a local anesthetic or a pharmaceutically acceptable salt there of on or adjacent to an exterior surface of the wound, wherein said pharmaceutically acceptable drug formulation is contained in a patch.

2. The method of claim 1, wherein the wound resulted from a surgical procedure.

3. The method of claim 2, wherein the surgical procedure is selected from the group consisting of laparoscopy, hemiaplasty, breast biopsy, and excision of subcutaneous tumors.

4. The method of claim 2, wherein the surgical procedure is selected from the group consisting of hemiaplasty and laparoscopy.

5. The method of claim 1, wherein the local anesthetic is selected from the group consisting of lidocaine, tetracaine, bupivacaine, prilocaine, mepivacaine, procaine, chloroprocaine, ropivacaine, dibucaine, etidocaine, and benzocaine or a mixture thereof.

6. The method of claim 1, wherein the local anesthetic is lidocaine.

7. The method of claim 1, wherein the pharmaceutically acceptable topical drug formulation does not comprise a penetration enhancer.

8. The method of claim 1, wherein the pharmaceutically acceptable topical drug formulation is covered with a dressing after the application step.

9. The method of claim 1, wherein the patch is a type selected from the group consisting of monolithic drug-in-adhesive, multi-laminate drug-in-adhesive, matrix, and reservoir.

10. The method of claim 1, wherein the patch is applied daily after a surgical procedure.

\* \* \* \* \*

UNITED STATES PATENT AND TRADEMARK OFFICE
CERTIFICATE OF CORRECTION

PATENT NO.    : 6,383,511 B1
DATED         : May 7, 2002
INVENTOR(S)   : R. Douglas Cassel It is certified that error appears in the above-identified patent and that said Letters Patent is hereby corrected as shown below:

Column 10,
Line 9, change "there of" to -- thereof --;
Lines 17 and 20, change "hemiaplasty" to -- herniaplasty --.

Signed and Sealed this

Twenty-fourth Day of June, 2003

JAMES E. ROGAN
*Director of the United States Patent and Trademark Office*